United States Patent
Zhai

(10) Patent No.: US 11,627,942 B2
(45) Date of Patent: *Apr. 18, 2023

(54) COLOR DOPPLER IMAGING WITH LINE ARTIFACT REDUCTION

(71) Applicant: Siemens Medical Solutions USA, Inc., Malvern, PA (US)

(72) Inventor: Liang Zhai, Castro Valley, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/931,928

(22) Filed: Sep. 14, 2022

(65) Prior Publication Data
US 2023/0000468 A1 Jan. 5, 2023

Related U.S. Application Data

(60) Continuation of application No. 16/044,885, filed on Jul. 25, 2018, now Pat. No. 11,478,224, which is a division of application No. 14/195,715, filed on Mar. 3, 2014, now Pat. No. 10,058,305.

(51) Int. Cl.
*A61B 8/00* (2006.01)
*A61B 8/08* (2006.01)
*A61B 8/06* (2006.01)

(52) U.S. Cl.
CPC ............ *A61B 8/488* (2013.01); *A61B 8/5269* (2013.01); *A61B 8/06* (2013.01)

(58) Field of Classification Search
CPC .......... A61B 8/5269; A61B 8/488; A61B 8/06
See application file for complete search history.

(56) References Cited

U.S. PATENT DOCUMENTS

| | | | |
|---|---|---|---|
| 6,312,381 B1 | 11/2001 | Knell et al. | |
| 10,058,305 B2 * | 8/2018 | Zhai | A61B 8/5269 |
| 11,478,224 B2 * | 10/2022 | Zhai | A61B 8/488 |
| 2010/0036249 A1 | 2/2010 | Clark | |
| 2011/0054316 A1 | 3/2011 | Kristoffersen et al. | |

* cited by examiner

*Primary Examiner* — Rajeev P Siripurapu

(57) ABSTRACT

Color Doppler imaging with line artifact reduction is provided in multi-beam scanning. Doppler estimates representing the same spatial location but calculated from spatially distinctive transmit beam groups are combined through weighted linear interpolation. Methods of calculating the linear interpolation weights are provided based on geometric relationships and optimization functions. Complete overlapping and superposition among receive beams in the interpolation region are not required. Partial interpolation among the receive beams, where only the estimates of the outer receive scan lines may overlap and be interpolated while estimates for scan lines closer to the transmit scan line are not interpolated, allowing for more rapid frame rate.

21 Claims, 6 Drawing Sheets

Artifact corrected beams

Artifact corrected beams

COLOR DOPPLER IMAGING WITH LINE ARTIFACT REDUCTION

RELATED CASE

This application is a continuation of U.S. application Ser. No. 16/044,885, filed Jul. 25, 2018, which is a divisional of U.S. application Ser. No. 14/195,715, filed Mar. 3, 2014, the disclosures of which are incorporated herein by reference.

BACKGROUND

The present embodiments relate to color Doppler, color flow, or other motion imaging using ultrasound. In particular, higher frame rate color motion imaging is provided with reduced line artifacts.

Parallel receive beam formation may increase ultrasound imaging frame rate. However, parallel receive beamformation may introduce line artifacts in color Doppler images due to the misalignment between the transmit and receive beams. Spatial filtering is typically used to overcome the line artifact, but spatial filtering may degrade the resolution. When the number of parallel receive beams per transmit beam increases for more rapid scanning, the line artifact becomes more severe, and eventually may not be managed with spatial filters. Though advanced modern ultrasound systems are capable of processing a large number of parallel receive beams, line artifact limits the number of parallel receive beams in color Doppler imaging (e.g., limited to four parallel receive beams). To increase the frame rate, color images either lack details due to spatial smoothing or show too much line artifact.

In one approach to address this dilemma, overlapping beams acquired from two adjacent transmit groups are linearly interpolated. The linear interpolation of the velocity estimates may be effective when all the receive beams are well covered by the transmit beams. Complete overlap in the receive beams between adjacent transmit beam groups is used, but complete overlaps may limit the frame rate. The linear interpolation is limited to pairs of collinear receive beams. Also, when the energy differences among receive beams are large due to insufficient transmit beam coverage, there may be periodic color dropout between transmit groups.

BRIEF SUMMARY

By way of introduction, the preferred embodiments described below include a method, instructions and systems for color imaging with line artifact reduction in multi-beam scanning. Doppler estimates representing the same spatial location but calculated from spatially distinctive transmit beam groups are combined through weighted linear interpolation. The linear interpolation weights are calculated based on geometric relationships and optimization functions. Complete overlapping and superposition among receive beams in the interpolation region are not required. Partial interpolation among the receive beams, where only the estimates of the outer receive scan lines may overlap and be interpolated while estimates for scan lines closer to the transmit scan line, are not interpolated allows for more rapid frame rate.

In a first aspect, a method is provided for color imaging with line artifact reduction. A first sequence of transmit beams is transmitted along a first scan line in a patient. Multiple first receive beams are received along each of multiple second scan lines in response to the first sequence of the transmit beams. A second sequence of transmit beams is transmitted along a third scan line in the patient, and multiple second receive beams are received along each of multiple fourth scan lines in response to the second sequence of the transmit beams. At least some of the second lines and fourth scan lines are in an overlapping region. First Doppler values are estimated from the first receive beams for each of the second scan lines, and second Doppler values are estimated from the second receive beams for each of the fourth scan lines. A processor interpolates first Doppler values with second Doppler values as a function of first and second weights. The first and second weights are determined as a function of a first sum to zero and a second sum to one. A Doppler image is generated as a function of the interpolated first and second Doppler values.

In a second aspect, a non-transitory computer readable storage medium has stored therein data representing instructions executable by a programmed processor for color imaging with line artifact reduction. The storage medium includes instructions for acquiring velocity estimates from different sequences of multiple simultaneous receive beam scanning for different ensembles of receive scan lines where the receive scan lines of the different sequences are in an overlapping region of a patient, interpolating the velocity estimates from the different sequences together for the overlapping region, where the interpolating is a function of weights based on distances of the receive scan lines from respective transmit beams, the interpolating performed for less than all of the receive scan lines, and generating a color flow image from the interpolated velocity estimates and velocity estimates without interpolation.

In a third aspect, a method is provided for color imaging with line artifact reduction. First receive multi-beams are formed with at least three spatially distinct scan lines from a first transmit sequence, and second receive multi-beams are formed with at least three spatially distinct lines from a second transmit sequence. The second transmit sequence is spatially distinct from the first transmit sequence. Third receive multi-beams are formed with at least three spatially distinct lines from a third transmit sequence. The third transmit sequence is spatially distinct from the first and second transmit sequences. Flow values are estimated from the first receive multi-beams, the second receive multi-beams, and the third receive multi-beams. A processor combines the flow values from the first, second, and third multi-beams as a function of weights. The weights are determined as a function of first, second, and third relative position of the spatially distinct scan lines to transmit scan lines of the first, second, and third transmit sequences, respectively. An image is generated as a function of the combined flow values.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

The line artifact when using parallel receive beams in color Doppler imaging may be dealt with, allowing improvement of frame rate while maintaining detail. Flow estimates of receive beams from different transmit beam groups are interpolated to correct the line artifact in color Doppler imaging. The velocity estimate bias that introduces line artifact may be corrected using multiple estimates, including estimates from three or more overlapped transmit beam groups. Massive parallel receive beams, such as for volume imaging, may be used in color Doppler imaging to achieve high frame rate and fine details without line artifact. Collinearity of receive beams that are acquired from different transmit groups is not required for the interpolation, which provides flexibility in beam positions. The interpolation may be performed for only sub-groups of estimates. Partial correction while maintaining good image quality may be used to increase frame rate. To deal with color dropout due to energy variation among the receive beams, beam dependent energy gain adjustment or compensation can be applied. Within a transmit beam group, the gain adjustment applied to individual receive beams is either a fixed value or a depth dependent vector.

Compared to previous approaches, a more flexible mechanism deals with the line artifact problem in color Doppler images when using a large number of parallel receive beams. Firstly, completely overlapping the receive beams from adjacent transmit beam groups are not required as either superimposed or staggered beam positions will work. Secondly, interpolation among more than two beam groups may be used. Thirdly, partial correction while still achieving a high image quality may be used. Fourthly, the approach may be implemented in volume imaging. Finally, the color dropout due to insufficient transmit beam coverage may be reduced.

For one-dimensional probes, the line artifacts may be reduced while still providing multiple times higher frame rates than without parallel receive and still providing details comparable to images without parallel receive. Due to the high frame rate, better hemodynamics visualization of flow may be provided for color Doppler imaging.

Figure 1:
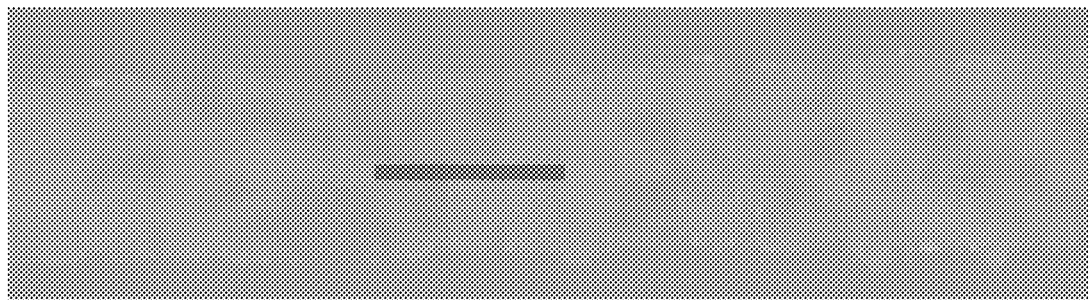
FIG. 1 is an example flow region or region of interest of a Doppler velocity image with line artifact due to multi-beam receive operation.

FIG. 1 demonstrates line artifacts in a color Doppler velocity image. The image is a magnified extract of a tubular flow region in a color Doppler velocity image. The image is acquired on a flow phantom with a Siemens SC2000 ultrasound system and 9L4 transducer using eight parallel receive beams per transmit. No interpolation is provided. The brightness of red color in FIG. 1 represents the estimated velocities. Color line artifacts appear as the regularly spaced vertical bands. The color line artifacts are created due to misalignment between transmit and receive beams.

Figure 2:
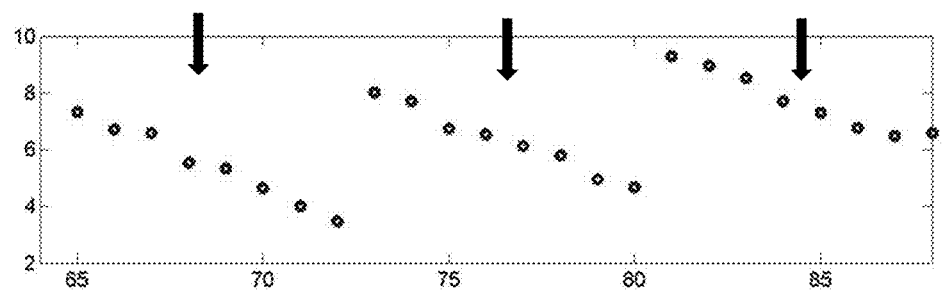
FIG. 2 shows an example of velocity bias by location for multi-beam groups.

FIG. 2 plots samples of the velocity data along the horizontal line in FIG. 1. The arrows indicate the transmit beam locations. A beam group pattern is shown in the normalized velocities. The further the receive beam is away from the corresponding transmit beam, the more deviation occurs in the velocity estimate from that of the velocities for the center beams, which are indicated by the blue arrows. The azimuth spacing of the receive scan line locations from the corresponding transmit scan line alters the amount of bias introduced into the estimate of velocity, causing the line artifact where the bias switches sign between groups of receive scan lines.

Figure 3:
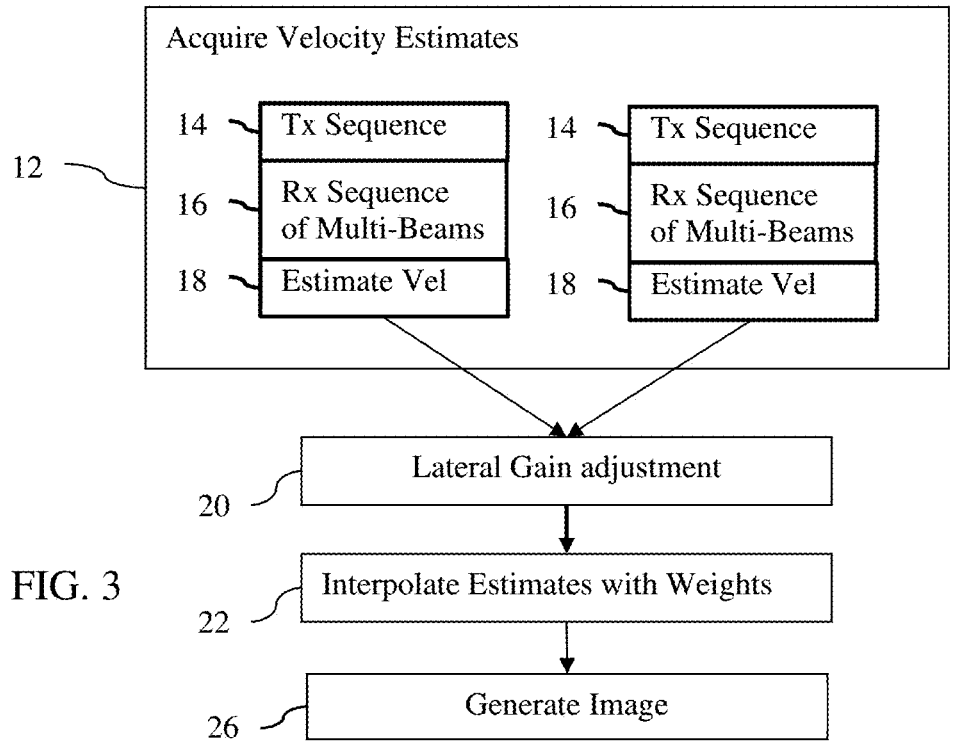
FIG. 3 is a flow chart diagram of one embodiment of a method for color imaging with line artifact reduction.

FIG. 3 shows one embodiment of a method for color imaging with line artifact reduction. By using linear interpolation, the line artifact may be reduced or eliminated while still benefiting from frame rate increase due to multi-beam receive. For interpolation, complete overlap with only pairs of estimates for interpolation may unnecessarily limit the scanning and/or frame rate benefits. By solving for the weighting based on two or more relationships of the weights, linear interpolation in various situations may be provided rather than requiring complete overlap of collinear lines of estimates.

Figure 11:
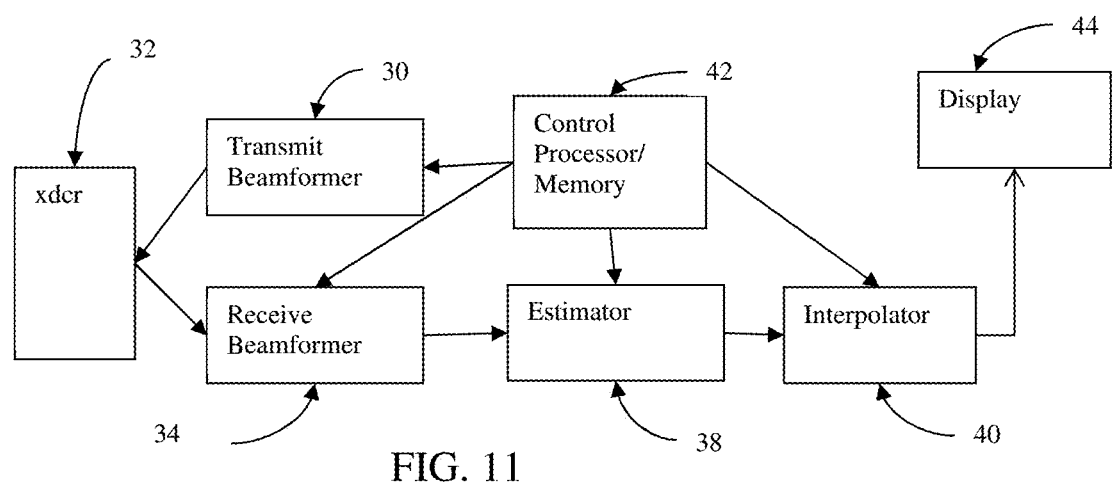
FIG. 11 is a block diagram of one embodiment of a system for color imaging with line artifact reduction.

The method of FIG. 3 is implemented by or on the system of FIG. 11, a processor, a workstation, a computer, or a different system. The method is performed by a medical diagnostic ultrasound imaging system. In other embodiments, the ultrasound data are acquired in real-time by an ultrasound scanner and other acts are performed in real-time or a different time by a computer, the ultrasound scanner or another device.

Additional, different or fewer acts may be provided. For example, acts 14, 16, and 18 are repeated more than twice. As another example, act 20 and/or 26 are not provided. In yet another example, acts for spatial and temporal filtering are included.

The acts are performed in the order shown or other orders. Acts 14, 16, and 18 are for acquiring flow estimates from groups of simultaneous receive lines. An ensemble of a transmit event and a parallel or multi-beam receive event occur to scan an ensemble region once. A sequence of such transmit and receive events is used to acquire samples for generating a given estimate. Any number of estimates may be generated. The acts are repeated to scan at a different location with or without overlapping of the scan region for given pairs of ensembles. Data from ensemble or sequences of scanning with an ensemble is collected prior to scanning for another ensemble, but interleaving in any pattern may be used. Different ensembles of transmit and responsive receive events are used to scan different portions of the field of view or region of interest. The acts 14 and 16 may be performed for different ensembles before or in parallel with performing acts 18 for other or the same ensembles.

In act 12, flow data are acquired. The flow data are velocities in FIG. 3, but may also or alternatively include energy (e.g., power) or variance.

The flow data are acquired by scanning a patient. The resulting scan data may be processed in real-time to generate an image. Alternatively, the scan data are saved and/or transmitted. The saved data are loaded from memory or received via a transmission for processing.

To acquire the flow data, the patient is scanned to acquire different sets of receive beams in act 16 responsive to spatially distinct transmissions of act 14. For example, with three or more different collinear receive beams, the three or more collinear receive beams are responsive to spatially distinct transmissions. The different ensembles (i.e., transmit beams along a given transmit scan line and corresponding multiple beams received along multiple receive scan lines in response to the transmit beams) cover overlapping regions. Part of the regions covered by the receive scan lines are covered by more than one ensemble. There may be complete overlap, such as where half of one ensemble is covered by half of another ensemble and the other half is covered by half of yet another ensemble. The overlap may be incomplete, such as where less than all of the region scanned by a given ensemble (transmit beam and responsive receive beams) is scanned by another ensemble. For example, ¼, ⅛ or other portion less than ½ is covered by an equal or unequal, but less than ½, portion of two surrounding (immediately adjacent) ensembles. In some of the examples below, the overlapping coverage is with collinear or co-located receive beams from different ensembles. In other embodiments, one or more of the receive scan lines from different ensembles are not collinear, but may still be interpolated.

Figure 4:
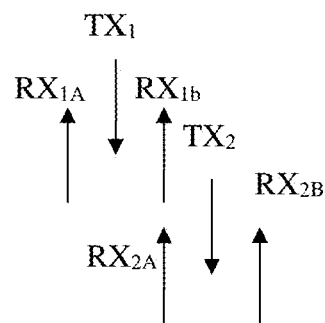
FIG. 4 is a graphical representation of one embodiment of transmit and receive beam interrelationships.

To acquire estimates for a same location from different transmit scan lines, two or more different ensembles are positioned to scan an overlapping region. Referring to FIG. 4, multiple non-collinear receive beams ($RX_{1A}$ and $RX_{1B}$, and $RX_{2A}$ and $RX_{2B}$) are formed in parallel or substantially simultaneously in response to each transmit firing ($TX_1$ and $TX_2$, respectively) of two ensembles (1 and 2). The set of spatially distinct beams formed in parallel is called non-collinear multi-beam or multi-beam (i.e., an ensemble of simultaneous receive scan lines).

As the number of beams in a multi-beam increases (e.g., three or more), the transmit beam is wider to adequately insonify the locations of the receive beams. The wider transmit beam may cause a decrease in resolution, increase in artifacts and decrease in signal-to-noise ratio (SNR). A given scan region may be scanned more rapidly with multi-beam, resulting in a greater frame rate.

In the example of FIG. 4, one receive beam ($RX_{2A}$) from one transmit event of an ensemble is collinear with another receive beam ($RX_{1B}$) from another transmit event of an ensemble. There is a ½ overlap in the transmit beams and/or ensemble coverage. With more than two receive beams and corresponding scan lines in an ensemble, more than one scan line per pair of ensembles may be collinear or in an overlapping region whether collinear or not.

At each transmit event (e.g., $TX_1$ or $TX_2$) of act 14, the transmit beamformer sends a beam. FIG. 4 shows two transmit beams generated at different times (different ensembles), represented by vertical position in the illustration of FIGS. 4 and 6-10. Each transmit beam is focused (i.e., converging wave front), unfocused (planar wave front) or defocused (diverging wave front) and propagates along a particular nominal transmit beam axis or transmit line.

At each receive event of act 16, the receive beamformer receives echoes from the object, and forms multiple beams in parallel. FIG. 4 shows two spatially distinct transmit events, and two receive beams formed in parallel or substantially simultaneously with each other in response to each transmit event. Three or more (e.g., 8, 16, 32, hundreds, or other number) receive beams may be formed, including with or without a receive beam along the transmit line or collinear with the transmit beam. Each receive beam is dynamically focused along a particular nominal receive beam axis or receive scan line. The receive beams formed in parallel as part of an ensemble are not collinear. The non-collinear beams of a receive multi-beam have different delays profiles. The remaining receive beamforming or echo shaping parameters such as aperture center, aperture width, apodization type, receive filter center frequency, bandwidth and spectral shape, may be the same or different.

FIG. 4 shows the receive multi-beams distributed in a plane, such as along an azimuth dimension with depth. The format shown is linear where the receive scan lines are parallel. In other embodiments, sector, Vector®, or other formats of the receive and/or transmit scan lines may be used. Three-dimensional or volume scanning may be provided where the scan lines are distributed in azimuth and elevation, such as using a wobbler or multi-dimensional transducer array.

Azimuth is along one dimension of the transducer array, such as the length. Elevation is along another, such as an orthogonal dimension of the transducer array (e.g., width). Depth or range is orthogonal to the face of the array or the distance along scan lines from the array.

The transmit and corresponding receive events are repeated to sample the region in space and in time. To sample the object in space, different ensembles with non-collinear transmit beams are used. Different portions of the scan region are sequentially scanned, as represented by the repetition of acts 14 and 16 in FIG. 3. FIG. 3 shows two ensemble regions being scanned, but three or more may be scanned. Any number of spatially different ensembles and corresponding ensemble scan regions may be used, such as the entire scan region, region of interest, or field of view being covered by 10-50 overlapping ensemble regions.

To sample the object in time, collinear events with identical beamforming and pulse shaping parameters are used. For example, for each color flow mode line, multiple collinear events uniformly distributed in time are used to obtain a collection of samples along each receive scan line at a pulse repetition frequency. A sequence of transmissions and receptions of an ensemble is performed to acquire the samples representing the same ensemble region over time. The collection is used to estimate a given parameter value (e.g., velocity value) for the represented locations. A moving window may be used to estimate a sequence of flow data acquired by transmitting and receiving in the ensemble to the same locations at different times.

Each ensemble is repeated over time to acquire sufficient samples for estimating motion for a given ensemble region. Different ensembles are being used to scan different, overlapping regions. This results in samples for estimates for each ensemble region where some of the resulting estimates from different ensembles are for the same location.

In act 18, motion data are estimated for each of a plurality of locations. The estimates are created along each of the receive scan lines for each given ensemble. For a given ensemble, temporal repetition of the transmission and multi-beam reception provides samples for estimating flow. Flow values are estimated for locations along each of the receive scan lines from a sequence of receptions along the scan lines. This estimation is repeated for each ensemble region, so estimates are provided for multiple scan lines of different ensemble regions.

The scanning may be performed a plurality of times in each ensemble region and a plurality of times in sequence across the ensembles to cover the entire scan region. The acts are repeated to scan different portions of the region of interest.

Scanning at different times acquires spatial samples associated with flow or motion. Any now known or later developed pulse sequences may be used. A sequence of at least two (flow sample count) transmissions is provided along each receive scan line. Any pulse repetition frequency, flow sample count, and pulse repetition interval may be used. The transmissions along one line(s) may be interleaved with transmissions along another line(s). With or without interleaving, the spatial samples for a given time are acquired using transmissions from different times. The estimates from different scan lines may be acquired sequentially, but rapidly enough to represent a same time from a user perspective. Multiple scans are performed to acquire estimates for different times.

The received spatial samples may be clutter filtered. The clutter filtering is to condition signals in the pulse sequence for estimating motion at a given location and time. A given signal may be used for estimates representing different times, such as associated with a moving window for clutter filtering and estimation. The clutter filter removes samples associated with slow or fast movement to isolate tissue motion or fluid motion. Different filter outputs are used to estimate motion for a location at different times.

The echo responses to the transmissions of the sequence are used to estimate velocity, clutter filtered or unfiltered energy (power), and/or variance at a given time. Color data are generated from the spatial samples. Any motion data may be generated, such as velocity, energy (power), and/or variance. Doppler processing, such as autocorrelation, may be used. In other embodiments, temporal correlation may be used. Another process may be used to estimate the flow data. Color Doppler parameter values (e.g., velocity, energy, or variance values) are estimated from the spatial samples acquired at different times. "Color" is used to distinguish from spectral Doppler imaging, where the power spectrum for a range gate is estimated. The change in frequency or phase between two samples for the same location at different times indicates the velocity. A sequence of more than two samples may be used to estimate the color Doppler parameter values. Estimates are formed for different groupings of received signals, such as completely separate or independent groupings or overlapping groupings. The estimates for each grouping represent the spatial location at a given time.

The estimation is performed for the different sampled spatial locations. For example, velocities for the different locations in a plane are estimated from echoes responsive to the scanning. Multiple frames of flow data may be acquired to represent the region of interest at different times, respectively. Motion values are estimated for each of the receive beams for each of the different ensembles.

Figure 5:
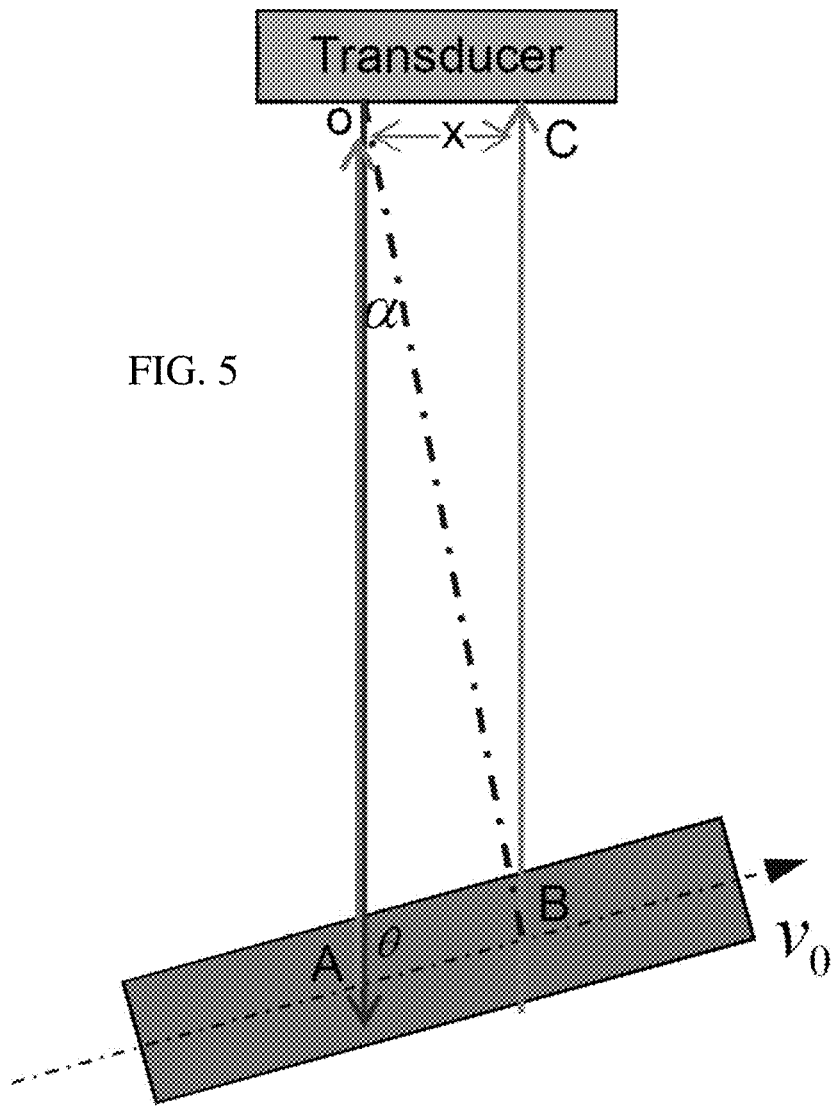
FIG. 5 shows an example position relationship between two parallel or simultaneous receive beams and a transmit beam.

FIG. 5 shows the acoustic Doppler effect associated with estimating velocity using multi-beam. Two simultaneous receive beams are shown at OA (i.e., same scan line as the transmit beam) and at CB (offset from OA by distance x). The Doppler shift represents the velocity or velocity is calculated from the Doppler shift. The Doppler shift, $\Delta f_A$, measured at point A is given by:

$$\Delta f_A = \frac{2v_o f_o}{c} \cos\theta \qquad (1)$$

where the pulse center frequency is $f_0$, the angle between the flow and transmit line (OA) is $\theta$, and the constant flow velocity (true velocity) is $v_0$. $\Delta f_A$ is a velocity estimate without bias due to beam misalignment. When the receive beam is not aligned with the transmit beam, such as for receive beam BC, a bias is introduced. The angle between OA and OB is $\alpha$. The Doppler shift measured at point B is derived as:

$$\Delta f_B = \frac{2v_o f_o}{c}(\cos\theta + \cos(\alpha + \theta)) \qquad (2)$$

As $\alpha$ is very small, $\Delta f_B$ may be further expanded around $\theta$. Below is a Taylor expansion, resulting in:

$$\Delta f_B = \frac{2v_o f_o}{c}\left(\cos\theta - \frac{\alpha}{2}\sin\theta + O(\alpha^2)\right) \qquad (3)$$

Equation 3 may be approximated as:

$$\Delta f_B \cong \Delta f_A - \left(\frac{1}{2}\Delta f_A \cdot \tan\theta\right) \cdot \alpha. \qquad (4)$$

The estimates for receive beams spaced from the transmit beams include a bias term, so are not an accurate representation of the flow at location B. The estimates for these receive beams are weighted to counteract the bias in the interpolation of act 22.

Prior to interpolation in act 22, Doppler energy estimates, such as filtered energy and unfiltered energy, may be adjusted in act 20 to compensate for the energy variation among receive beams due to their distance from the transmit beam location. The gain adjustment is performed for each receive beam so that the energy differences among receive beams due to their relative location to the transmit beam are equalized. The energy estimates may be used as part of the thresholding process in Doppler imaging. Thresholds are applied to Doppler parameters such as velocities, energies and variances, or a function of these parameters to decide if a given estimate is a valid flow signal. For example, a low velocity threshold is applied. Velocities below the threshold are removed or set to another value, such as zero. As another example, where the energy is below a threshold, the velocity value for the same spatial location is removed or set to another value, such as zero. Alternatively, the estimated velocities are used without thresholding.

Where the receive beam is sufficiently far from the transmit beam of a given ensemble, its energy can be significantly lower than those closer to the transmit beam, though the corresponding velocity estimates may be valid. During thresholding process, the low energy of beams far away from the transmit beam can cause the corresponding Doppler estimates to be rejected as flow, so can produce periodic color dropout in the image. To address the potential beam dropout when the energy differences between the receive beams are large, the gain of each beam or some beams may be adjusted based on its relative location to the transmit beam. Gain adjustment may be avoided or limited by sufficient or reasonable transmit beam coverage for all the receive beams.

The amount of gain adjustment for each beam can be predetermined through acoustic modeling, phantom measurements, or other methods, such as assuming a simplified mathematical function, like Gaussian or sinc, for the lateral energy profile of the transmit beam and computing the adjustment values accordingly. For a given receive beam, the gain adjustment can be constant or depth varying.

In act 22, estimates from different ensembles are interpolated together. For example, Doppler velocities representing the same or adjacent locations, but estimated from different transmit beam and responsive receive multi-beams combinations are interpolated. A processor combines the estimates associated with the different sequences of scanning using spatially distinct or non-collinear transmit beams.

Any number of estimates may be combined. For example, estimates from three different ensembles are interpolated to provide an estimate for a given location. The estimates from the different sequences representing the same overlapping region or location are interpolated.

Interpolation may be implemented in different ways. In one embodiment, a linear interpolation is used. The estimates, such as velocity values, from each ensemble are separately weighted. The weighting is a multiplication, but can be implemented in forms of other functions, such as division or addition and subtraction in a logarithm domain. The results of the weighting are summed. Other functions than summing may be used. Special treatment on interpolating individual pixels may be considered based on the Doppler estimates or B mode information on those pixels. For example, when the filtered energy at a given pixel after lateral gain adjustment in one transmit group is lower than a threshold or significantly lower compared to estimates from those of other transmit beam groups, its contribution to the final output is zeroed or minimized. And the weights for Doppler parameters estimated from other transmit beam groups may be adjusted accordingly or simply rescaled to strictly or approximately satisfy a function of a first sum to zero and a second sum to one.

In Equation 4, the first term $\Delta f_A$ is the velocity estimate without bias. The second term shows the first order bias term, which is linearly proportional to the misalignment angle $\alpha$, and is the primary factor contributing to the beam group artifact. $\alpha$ is a real number, which may be either negative or positive. To eliminate or reduce the line artifact, receive beams from multiple transmit beam groups or ensembles are combined with relative weighting. N represents the number of ensembles or transmit beam/multi-beam receive groups, which have biased estimates represented as $\Delta f_{B1}$, $\Delta f_{B2}$, ... $\Delta f_{Bn}$. The final output estimate, $\Delta f_d$, of interpolation is represented as:

$$f_d = \Sigma_{i=1}^n c_i \Delta f_{B_i} = \Delta f_A \quad (5)$$

where $c_i$ are the group of weights applied to respective estimates from the ensembles.

To solve for the weights (i.e., coefficients $c_i$) used in the linear interpolation, two or more equations representing the relationships between the weights are used. In one embodiment, two sums of the coefficients are defined as the two equations, but other relationships may be used. Since the bias is linearly proportional to angle $\alpha$, receive beams with different $\alpha$ relative to their transmit beams can be combined to correct the bias. Thus, this angle is used in the solution for determining the weights. Greater angles result in greater bias, so the corresponding weight should be less for those estimates. Estimates for receive scan lines that are collinear with the transmit scan line should have the greatest weight as there is no bias from multi-beam. Using estimates from different sides of the ensembles relative to the respective transmit beams, the angles have opposite signs. For the linear interpolation, the sum of the weights should be 1. For example, the two equations are represented as:

$$\Sigma_{i=1}^n c_i \alpha_i = 0 \quad (6), \text{ and}$$

$$\Sigma_{i=1}^n c_i = 1 \quad (7)$$

Equations 6 and 7 indicate among all the receive beams, a least one receive beam is located on the opposite side of the corresponding transmit beam than another of the receive beams to its corresponding transmit beam, which means at least one $\alpha$ has different sign (+/−) compared to others.

For data acquired with a linear array, $\alpha$ is small and is proportional to x. As shown in FIG. 5, x is the distance from the transmit scan line to the receive scan line. For a flat, linear array, x is a distance between the origins of the scan line on the face of the transducer or a shortest distance. For curved or other arrays, x may be a distance between the transmit and receive scan lines at the region of interest, such as a shortest distance between transmit and receive scan lines in the flow tube. A distance over the curved surface or a distance between origins through the curve may be used. The value |x| and sign (+/−) represents the distance and side (left or right) of the receive scan line from the corresponding transmit scan line. Equations 6 and 7 may be rewritten to replace $\alpha$ with x, simplifying calculation. Equation 8 and 9 represent this replacement:

$$\Sigma_{i=1}^n c_i x_i = 0 \quad (8), \text{ and}$$

$$\Sigma_{i=1}^n c_i = 1 \quad (9)$$

where x is a real number. Equations 6 and 7 provide a solution for data acquired by phased or curvilinear arrays. Equations 8 and 9 make implementing this technique straightforward for linear arrays. These equations may be further simplified or normalized by the receive beam spacing or number of parallel receive beams per transmit independent of which type of array, such as phased or linear or curvilinear array, or the acoustic scanning format.

With proper coefficients, the final results combined from the estimates of the n beams shows no or reduced bias or line artifact as shown in Equation 5. The estimates with bias are weighted such that the interpolation results in removal of the bias in the resulting interpolated estimate. The biases are weighted so that the bias terms cancel each other out in combining or summing the weighted estimates.

Equations 6 and 7, or 8 and 9 may be solved. The weights are calculated as needed by a processor. Alternatively, the weights are pre-calculated for a given scan format. The pre-calculated weights are loaded from memory, such as looking up the weights given an application, user scan settings, or other indicator of the scan format.

The weights are determined for each estimate to be included in the interpolation. For the example of FIG. 4, two estimates corresponding to the two ensembles used to interpolate for the collinear scan lines $RX_{1A}$ and $RX_{2A}$ are weighted for a given depth and the results summed. In other examples, three or more estimates are to be weighted and summed together for the interpolation. The relative position of each receive scan line associated with a given estimate to the respective transmit scan line position is used for determining the weight, such as using equations 8 and 9 with the distance x or equations 6 and 7 with the angle $\alpha$. The distances or angles of the receive scan lines to corresponding transmit scan lines are used to determine the weights.

Any solution may be used. When using two receive beams (e.g., FIG. 4) to overcome the line artifact, equations 8 and 9 provide a unique solution for the coefficients ($C_1$ and $C_2$) once the relative positions of the beams are defined. In the example of FIG. 4, both distances are equal ($RX_{1b}$ from $TX_1$ and $RX_{2a}$ from $TX_2$), but with opposite signs (different sides of the respective transmit scan lines). The unique solution is 0.5 and 0.5. As another example, one receive scan line is twice the distance from the corresponding transmit scan line than the other receive scan line is from its corresponding scan line. The unique solution for weighting the estimates becomes 0.33 and 0.67, with the 0.67 applied to the estimate for the scan line closer to the transmit line, cancelling out the larger bias of the receive scan line farther from it's transmit scan line.

Figure 9:
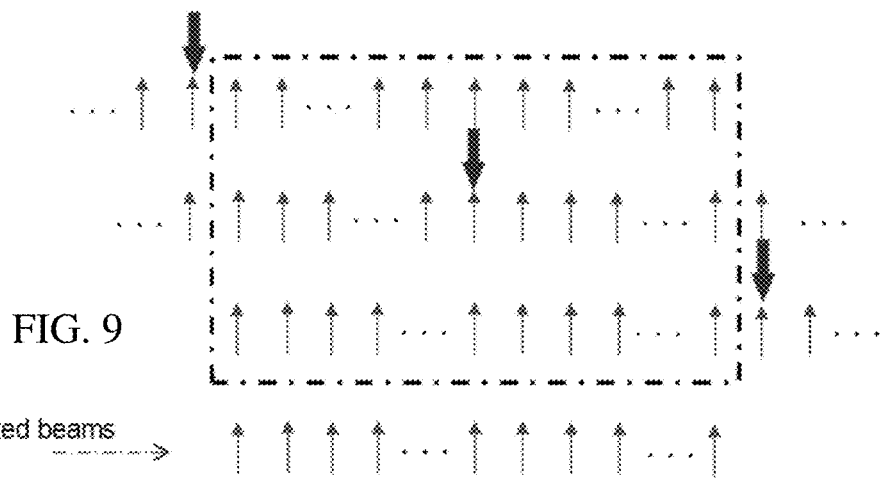
FIG. 9 illustrates an example of velocity interpolation of sets of three receive beams.

For interpolating more than two estimates, an optimization function is used. Equations 6 and 7, or 8 and 9 may be solved for situations that interpolate estimates from receive beams from three or more transmit beam groups or ensembles. FIG. 9 shows an example using three transmit beam groups.

For interpolation from three or more estimates, the solution that satisfies equations 6 and 7, or 8 and 9 will not be unique. Any solution may work when the signal-to-noise ratio in all the estimates are high or not below a threshold level. Alternatively, an optimization with an objective function is used. The coefficients may be optimized to ensure a robust and high quality imaging configuration. The objective function incorporates beam energy, velocity, beam spacing, and/or other consideration of image quality. The objective function may be defined and optimized to solve for $c_i$. Any optimization with any objective function may be provided. In one embodiment, the energy corresponding to the velocity estimates is used as the objective function. The linear interpolation of filtered energy before lateral beam gain adjustment is maximized. A function of maximum energy with equations 8 and 9 as conditions on the solution of the maximum energy is solved. For example, the function is: arg $\max_{c_i} c_i e_i, c_i$ subject to the conditions of equations 8 and 9. This objective function assumes Doppler data associated with higher filtered energy have more robust velocity estimates. Other functions, such as a minimization and/or with additional terms, may be used.

FIGS. 6-10 show example ensemble relationships for interpolation of estimates. The downward, larger arrows represent transmit scan lines and the group of upward, narrower arrows just below each given transmit represent the simultaneous multi-beam receive scan lines. Each ensemble is shown on a different horizontal position to show sequence in scanning. Multiple transmit and receive events are performed for a given ensemble before doing so for the next ensemble. The arrows only indicate the locations of beams, which may include multiple flow samples at each location. Doppler parameters, such as velocity, filtered energy, unfiltered energy, and/or variance are estimated from the received samples for each ensemble, resulting in groups of flow estimate values representing each of the receive scan lines. The artifact corrected beams at the bottom of the figure are interpolated results. The estimates from the scan lines of two or more different ensembles are interpolated together with weights, forming estimates for the artifact corrected beams.

Figure 6:
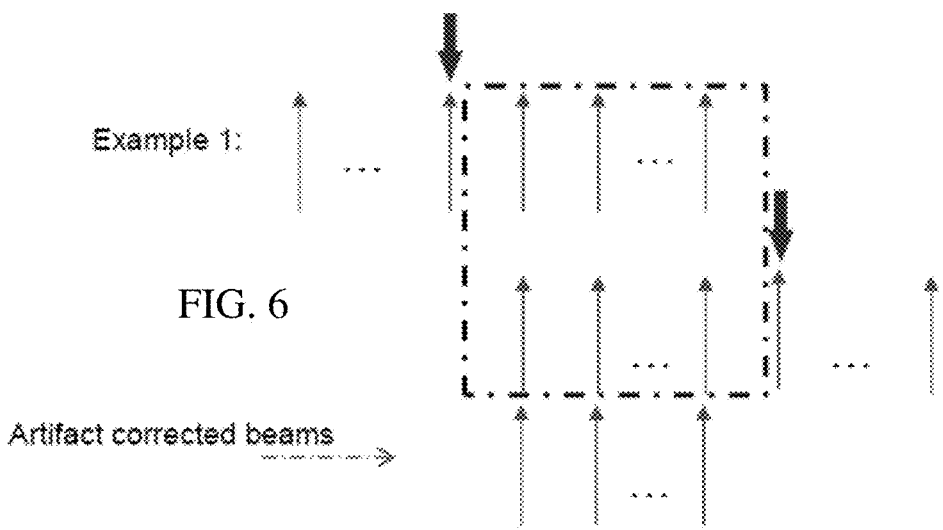
FIG. 6 illustrates an example of velocity interpolation along an odd number of multiple collinear receive beams.
Figure 7:
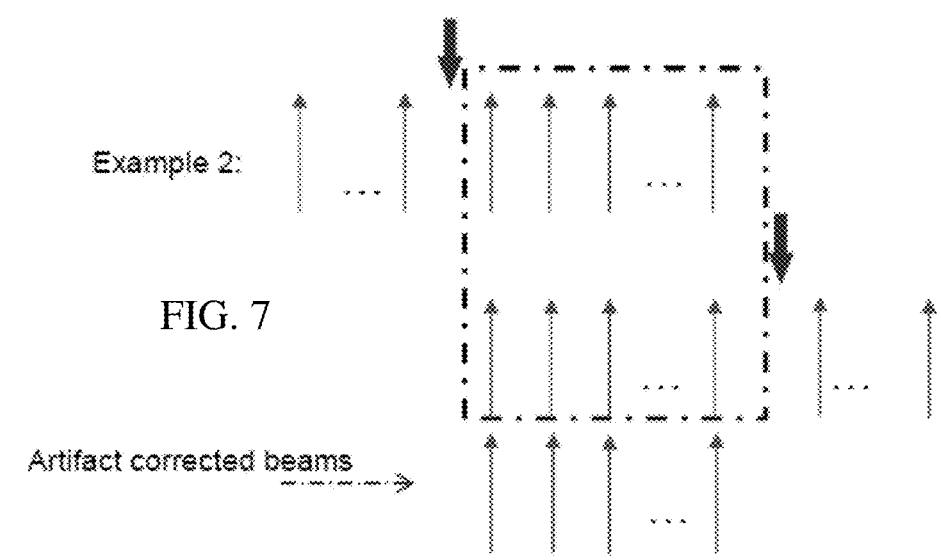
FIG. 7 illustrates an example of velocity interpolation along an even number of multiple collinear receive beams.

FIGS. 6 and 7 demonstrate some examples that use two adjacent beam transmit groups to correct the velocity biases and/or line artifact. The receive scan lines in the overlap region (dash-dot box) are collinear, precisely superimposing on each other. Estimates for collinear receive scan lines are interpolated (weighted and summed). In FIGS. 6 and 7, the interpolation is of two estimates per location, so the solution for the weights is unique.

In the example of FIG. 6, an odd number of receive scan lines is provided. As a result, one of the receive scan lines is collinear with the transmit scan line. The estimates for this line do not have bias. The dashed box represents the overlapping region in which interpolation is to occur for a given set of ensembles. Since there is no bias for the receive scan line collinear with the transmit scan line, interpolation is not performed. In a scan of a region of interest, the receive scan lines on the right are also in an overlapping region with another ensemble, leaving just the estimates of the receive scan line collinear with the transmit scan line as not interpolated in forming the image.

In the example of FIG. 7, an even number of receive scan lines are provided in the ensemble or per transmit. In this example, half of the receive scan lines are in the overlap region or subject to some bias in the estimates. With another ensemble on the other side (not shown), all of the receive scan lines are in ensemble overlap regions and are to be interpolated. For ensembles at an edge of the overall region of interest or scan region, some interpolation may not be provided.

Figure 8:
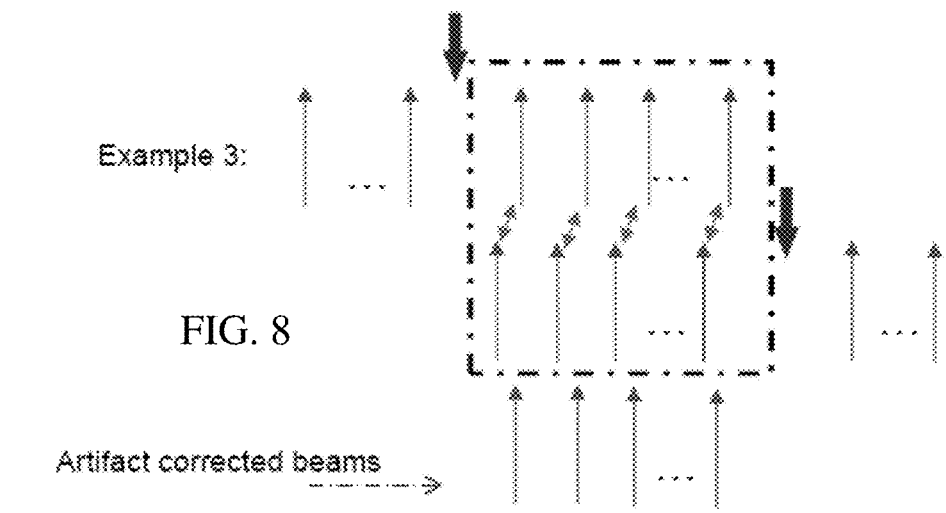
FIG. 8 illustrates an example of velocity interpolation along non-collinear receive beams.

FIG. 8 shows an example of interpolation where the estimates represent scan lines that are not collinear with each other. The receive scan lines are staggered from two adjacent beam groups, so estimates for a new line are computed in-between these staggered scan lines. The closest pairs or sets of receive scan lines are identified, and the corresponding estimates are interpolated together. The resulting estimates represent a line in-between the receive scan lines involved in the interpolation. Other groups for interpolation may be used, such as forming additional lines of estimates using interpolation from other more spaced apart lines. Such additional lines may be formed in the examples of FIGS. 6 and 7 as well.

FIG. 9 shows an example with three ensembles in the same overlap region. Each artifact created set of estimates is interpolated from three estimates corresponding to three collinear receive scan lines. In this example, a receive scan line collinear with a transmit scan line is included in the interpolation. In alternative embodiments, an even number of receive scan lines is used or no interpolation is provided and the estimates from the receive scan line that is collinear with the transmit scan line are used as artifact corrected estimates. To the left and/or right of the overlap region shown in FIG. 9, other overlap regions are created that include or do not include the receive scan lines collinear with the transmit scan lines shown adjacent to the overlapping region of FIG. 9. In other embodiments, four or more estimates (i.e., combining from four or more ensembles of multiple receive beams) are interpolated.

Figure 10:
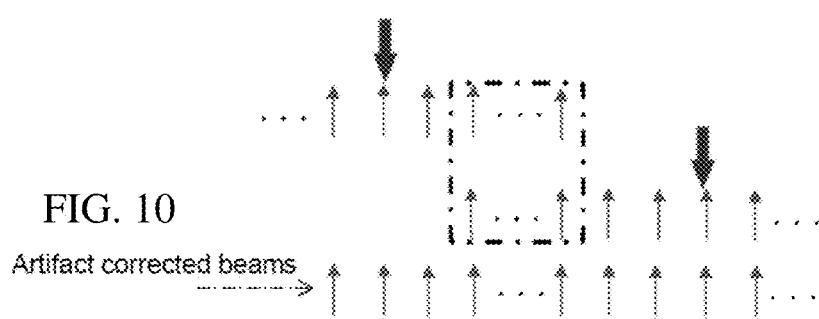
FIG. 10 illustrates an example of velocity interpolation for only a sub-set of the multiple receive beams.

FIG. 10 shows an example for increasing the frame rate while reducing the line artifact. As discussed for FIG. 2, the receive scan lines collinear with and near to the transmit scan line have no or little bias. The estimates for these receive scan lines may be used without interpolation. The overlap region only covers the receive scan lines of each ensemble farthest from the respective transmit scan line. For example, the center most one (shown in FIG. 6), two, three (shown in FIG. 10), or more receive scan lines of an ensemble are not involved in interpolation. The estimates for these center receive scan lines are used in imaging without interpolation with estimates from other ensembles. The interpolation is performed for less than all of the receive scan lines, whether an even or odd number of receive scan lines are used. The interpolation is performed for the estimates of the receive scan lines spaced further from the center.

By interpolation for a sub-set and not interpolating for another sub-set, less overlap of ensembles is used. This may result in scanning the entire region of interest, field of view, or scan region with fewer ensembles of simultaneous multi-beam receive, increasing frame rate. The biases for the non-interpolated estimates may be negligible. An incomplete beam interpolation may be used without sacrifice of the image quality.

These examples are for planar imaging. In volume imaging, a similar approach may be used. The receive scan lines are distributed in the volume (azimuth and elevation) rather than just the plane (azimuth). The scan pattern of ensembles provides for overlap in both azimuth and elevation, providing for interpolation of estimates along both the azimuth and elevation spaced receive scan lines. The line artifact may be reduced or eliminated in volume imaging using the weighted interpolation. By solving for the weights using the multi-equation solution with or without an objective function, a versatile approach may be provided for removal of the line artifact.

In act 26 of FIG. 3, a Doppler or other motion image is generated. For example, a color Doppler or color flow image is generated. Velocities are mapped to colors, and the colors are displayed. The flow information is displayed for regions of flow, such as where sufficiently (e.g., thresholded) high velocities and/or energies occur. For other locations, B-mode, other, or no data are used for the image. In one embodiment, the color flow image is a color overlay on a B-mode image. As an alternative to color, the flow estimates may be mapped to gray scale values. In yet other alternatives, the estimates are for moving tissue and a tissue Doppler image is generated.

The motion image is generated from at least some interpolated estimates. The motion values combined with weighted interpolation are used for some or all of the locations for which motion is displayed. The results of the interpolation include less bias, so the resulting image includes less line artifact. Where some estimates are not interpolated, the resulting image is generated with estimates resulting from the interpolation and estimates free of interpolation between ensembles. By interpolating for only a sub-set of receive scan lines, flow images with a greater frame rate may be provided.

Where the gain of the energy values is increased for some receive scan lines, drop-out may be avoided. The energy estimates resulting from interpolation are likely to have values above the energy cut-off due to the increase in gain. The result is velocity values not being removed for some locations, avoiding drop-out in the image.

In one embodiment, the image is generated as representing a plane within the patient, such as a scan plane. A sequence of images may represent the scan plane over time. The scanning and estimation is repeated to show the motion at different times. In another embodiment, the image represents a volume. Three-dimensional rendering, such as surface rendering, volume rendering, projection rendering (e.g., maximum value), or alpha blending, is performed from a given viewing using the motion estimates. Any now known or later developed three-dimensional rendering may be used. Multi-planar reconstructions (e.g., extracting a plurality of different imaging planes from volume information) may be used. An arbitrary planar image may be generated from estimates representing a volume.

FIG. 11 shows one embodiment of a system for color imaging with line artifact reduction. The system is an ultrasound imaging system, but other imaging systems using multiple receive may be used. In other embodiments, the system is a computer, workstation, server, or other processor for operating on scan data received over a network or loaded from memory.

The system includes a transducer 32, a transmit beamformer 30, a receive beamformer 34, an estimator 38, an interpolator 40, a display 44, and a control processor and memory 42. Additional, different or fewer components may be provided. For example, a scan converter is provided. As another example, the memory is separate from the processor 42. In yet another example, the processor 42 implements the interpolator 40.

The transducer 32 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof or any other now known or later developed array. The transducer elements transduce between acoustic and electric energies. The transducer 32 connects with the transmit beamformer 30 and the receive beamformer 34 through a transmit/receive switch, but separate connections may be used in other embodiments.

Two different beamformers are shown in the system 10, a transmit beamformer 30 and the receive beamformer 34. While shown separately, the transmit and receive beamformers 30, 34 may be provided with some or all components in common. Both beamformers connect with the transducer 32. The transmit beamformer 30 is a processor, delay, filter, waveform generator, memory, phase rotator, digital-to-analog converter, amplifier, pulser, switches, combinations thereof or any other now known or later developed transmit beamformer components. The transmit beamformer is configured as a plurality of channels for generating electrical signals of a transmit waveform for each element of a transmit aperture on the transducer 32. The waveforms have relative delay or phasing and amplitude for focusing, defocusing, or planar focusing of the acoustic energy. The transmit beamformer 30 includes a controller for altering an aperture (e.g. the number of active elements), an apodization profile across the plurality of channels, a delay profile across the plurality of channels, a phase profile across the plurality of channels and/or combinations thereof.

The transmit beamformer 30 is configured for broad beam transmit, such as spreading acoustic energy over an ensemble region for simultaneous receive beam formation. The broad beam is diverging (defocused, no focus, or focus behind the array or before the region of interest), converging (focus in or beyond the region of interest), or planar (infinite focus).

The receive beamformer 34 is a preamplifier, filter, phase rotator, delay, summer, base band filter, processor, buffers, memory, combinations thereof or other now known or later developed receive beamformer components. The receive beamformer 34 is configured into a plurality of channels for receiving electrical signals representing echoes or acoustic energy impinging on the transducer 32. Beamforming parameters including a receive aperture (e.g., the number of elements and which elements are used for receive processing), the apodization profile, a delay profile, a phase profile and combinations thereof are applied to the receive signals for receive beamforming. For example, relative delays and amplitudes or apodization focus the acoustic energy along one or more scan lines. A control processor controls the various beamforming parameters for receive beam formation. Beamformer parameters for the receive beamformer 34 are the same or different from the transmit beamformer 30.

The receive beamformer 34 includes one or more digital or analog summers operable to combine data from different channels of the receive aperture to form one or a plurality of receive beams. Cascaded summers or a single summer may be used. In one embodiment, the beamform summer is operable to sum in-phase and quadrature channel data in a complex manner such that phase information is maintained for the formed beam. Alternatively, the beamform summer sums data amplitudes or intensities without maintaining the phase information.

For simultaneous multi-beam, the receive beamformer 34 includes circuits, channels, memories, or other components for applying different delay or phase profiles to the same received data. Multiple receive beams for a respective multiple receive scan lines are formed in response to echoes from a transmit beam.

The estimator 38 is a general processor, digital signal processor, control processor, application specific integrated circuit, digital circuit, digital signal processor, analog circuit, combinations thereof or other now known or later developed processor for flow or motion estimation. The estimator 38 detects any of various characteristics, such as velocity, energy (i.e. power), and/or variance. A clutter filter may be provided for filtering the samples prior to estimation. A corner turning memory may be used to store the samples over time used to estimate flow for a given location. In one embodiment, the estimator 38 is a Doppler processor for estimating from the phase shift. A correlator or other processor may be used. The estimator 38 outputs estimates for each location. Separate estimates are provided for each ensemble of receive scan lines. Multiple samples for each location of each receive scan line are used to estimate the flow for a given time. The estimation may be repeated with a moving window to provide estimates over time for each location. The estimation is repeated for each ensemble, providing estimates for overlapping regions in response to different transmit scan line locations.

The interpolator 40 is a processor, circuit, digital circuit, field programmable gate array, digital signal processor, application specific integrated circuit, combinations thereof, multiplier, summer, buffer, or other device for interpolating or combining estimates. In one embodiment, the interpolator 40 is implemented by the control processor 42. The interpolator 40 is configured by hardware and/or software to combine estimates. The interpolator 40 and/or the control processor 42 are configured to determine the weights for the different estimates used in interpolation. Either calculation or look-up from memory is used.

The interpolator 40 combines estimates from collinear or non-collinear receive scan lines of different ensembles or spatially distinct transmit beam locations. The estimates are weighted with weights to remove line artifact. The weights account for the number of estimates to be combined for a given location and the spatial location for each estimate relative to the respective transmit scan line. Three or more estimates may be interpolated using two or more conditions of an objective function and optimization. Some estimates may not be interpolated, allowing for less overlap in the scanning and greater frame rate. The interpolation may be between estimates that are not associated with collinear receive scan lines.

A filter may be provided for spatial filtering. Any residual line artifact may be removed by spatial filtering. Since some of the line artifact is removed by the weighted interpolation, less spatial filtering may be needed. Alternatively, no spatial filtering is provided.

The estimates resulting from interpolation and/or passing through interpolation (i.e., not interpolated) are on a same acoustic or scan grid. This grid may match a display grid of the display 44. Alternatively, a spatial transformation or scan conversion aligns the estimates to the display grid. The data are output as an one-, two-, or three-dimensional representation on the display 44. Other processes, such as the generation of text or graphics may also be performed for generating an image on the display 44. For example, a display dynamic range is set, filtering in space and time using a linear or nonlinear filter which may be an FIR or IIR filter or table-based is provided, and/or the signal amplitude is mapped to display values as a function of a linear or non-linear map.

The control processor 42 is a general processor, digital signal processor, field programmable gate array, application specific integrated circuit, graphics processing unit, digital processor, analog processor, circuit, or combinations thereof. The control processor 42 interacts with one or more components to control the system. Alternatively or additionally, the control processor 42 performs part of the process, such as interpolating and/or determining weights used for interpolation.

As part of the image forming process, the control processor 42 sets a scan pattern or acquisition sequence, number of simultaneous receive beams, a number of sequential beams, a number of component beams compounded together, receive multiple beam parameters, combination function, weights for combination, combinations thereof, or other now known or later developed parameters for line artifact reduction in motion imaging using multi-beam.

The control processor 42, interpolator 40, or other component determines the weights used for interpolation. The weights are determined from looking up in a memory given a scan configuration or by solving one or more equations. For example, the control processor 42 uses the two sums of equations 6 and 7 or 8 and 9 to solve for weights. As another example, the control processor uses the two sums with an objective function to solve for the weights.

The instructions for implementing the processes, methods and/or techniques discussed above are provided on non-transitory computer-readable storage media or memories, such as a cache, buffer, RAM, removable media, hard drive or other computer readable storage media. The instructions are implemented on a single device, such as the control processor 42, or a plurality of devices in a distributed manner. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, filmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A system comprising:
a transmit beamformer configured to transmit a first sequence of transmit beams along a first scan line in a patient and to transmit a second sequence of transmit beams along a third scan line in the patient;
a receive beamformer configured to receive multiple first receive beams along each of multiple second scan lines in response to the first sequence of the transmit beams and to receive multiple second receive beams along each of multiple fourth scan lines in response to the second sequence of the transmit beams, at least some of the second lines and fourth scan lines in an overlapping region;
a Doppler processor configured to estimate first Doppler values from the first receive beams for each of the second scan lines and to estimate second Doppler values from the second receive beams for each of the fourth scan lines;
an interpolator configured to interpolate first Doppler values with second Doppler values as a function of first and second weights, respectively, and to determine both the first weight and the second weight by solving first and second functions, the first function including a first sum of the first weight multiplied by a first distance or angle of one of the second scan lines from the first scan line and the second weight multiplied by a second distance or angle of one of the fourth scan lines from the third scan line to zero and the second function including a second sum of the first and second weights to one; and
a display to display a Doppler image as a function of the interpolated first and second Doppler values.

2. The system of claim 1 wherein the receive beamformer is configured to receive at least three receive beams in response to each of the transmit beams of the first and second sequences, the at least some of the second and fourth lines being collinear in the overlapping region.

3. The system of claim 1 wherein the first and second Doppler values comprise velocities.

4. The system of claim 1 wherein the interpolator is configured to weight the first Doppler values with the first weight, weight the second Doppler values with the second weight, and sum results of the weighting.

5. The system of claim 1 wherein the interpolator is configured to determine with the first function including the first and second distances.

6. The system of claim 1 wherein the interpolator is configured to interpolate only for sub-sets of the first and second Doppler values corresponding to second and fourth scan lines spaced from the first and third scan lines, respectively, and not interpolate for first and second Doppler values corresponding to second and fourth scan lines along or closer to the first and third scan lines than the second and fourth scan lines of the sub-sets.

7. The system of claim 1 wherein the interpolator is configured to solving an objective function of a maximum of linearly interpolated energy estimates of the first receive beams and the second receive beams with the first and second functions being conditions for the solution.

8. The system of claim 1 wherein the interpolator is configured to interpolate the first and second Doppler values corresponding to second and fourth scan lines that are non-collinear together.

9. The system of claim 1 wherein the second and fourth scan lines are distributed in azimuth and elevation, and wherein the Doppler image comprises a rendered three-dimensional image.

10. The system of claim 1 wherein the Doppler image is a function of Doppler energy values with the adjusted gain and the first and second Doppler values.

11. A system comprising:
a Doppler processor configured to acquire velocity estimates from different sequences of multiple simultaneous receive beam scanning for different ensembles of receive scan lines where the receive scan lines of the different sequences are in an overlapping region of a patient;
a processor configured to solve first and second functions to determine weights, the first function including a first sum of the weights for a first of the different sequences multiplied by distances or angles of the receive scan lines from respective transmit beams for the first of the different sequences equal to zero and the second function including a second sum of the weights equal to one and configured to combine the velocity estimates from the different sequences together for the overlapping region, where the combination is a function of the weights and is performed for less than all of the receive scan lines; and
a display to display a color flow image from the combined velocity estimates and velocity estimates without combination.

12. The system of claim 11 wherein the Doppler processor is configured to estimate the velocity estimates for each of a plurality of locations represented by each of the receive scan lines of a respective sequence.

13. The system of claim 11 wherein the processor is configured to combine for the receive scan lines spaced further from respective transmit beams than for the receive scan lines spaced closer to the respective transmit beams and not combine for the receive scan lines spaced closer to the respective transmit beams than for the receive scan lines spaced further from the respective transmit beams.

14. The system of claim 11 wherein, in the color flow image, the velocity estimates adjacent to transmit scan lines are without the combination and the velocity estimates spaced further from the transmit scan lines than the velocity estimates adjacent to the scan lines adjacent are from the combination.

15. The system of claim 11 wherein at least some of the receive scan lines from the different sequences are collinear in the overlapping region.

16. The system of claim 11 wherein the processor is configured to weight the velocity estimates for a first one of the different sequences with the weights based on the distances or angles of the receive scan lines from the first one of the different sequences from respective transmit beams for the first one of the difference sequences and is configured to interpolate the velocity estimates corresponding to the receive scan lines that are non-collinear together.

17. The system of claim 16 wherein the processor is configured to weight the velocity estimates for a second one of the different sequences with the weights based on the distances or angles of the receive scan lines from the second one of the different sequences from respective transmit beams for the second one of the difference sequences and sum results of the weightings of the velocity estimates for the first and second ones of the different sequences.

18. The system of claim 11 wherein the processor is configured to determine the weights based on the distances.

19. The system of claim 11 wherein the processor is configured to determine the weights based on the angles.

20. The system of claim 11 the processor is configured to optimize for the weights of the first and second functions, the optimization being based on an objective function of a maximum of linearly combined energy.

21. An ultrasound system for artifact reduction in imaging from velocity estimates from different sequences of multiple simultaneous receive beam scanning for different ensembles of receive scan lines where the receive scan lines of the different sequences are in an overlapping region of a patient, the ultrasound system comprising:

a processor configured to solve first and second functions to determine weights, the first function including a first sum of the weights for a first of the different sequences multiplied by distances or angles of the receive scan lines from respective transmit beams for the first of the different sequences equal to zero and the second function including a second sum of the weights equal to one and configured to combine the velocity estimates from the different sequences together for the overlapping region, where the combination is a function of the weights and is performed for less than all of the receive scan lines;

wherein the imaging comprises a color flow image from the combined velocity estimates and velocity estimates without combination.

* * * * *